United States Patent [19]

Steer

[11] Patent Number: 5,531,725
[45] Date of Patent: Jul. 2, 1996

[54] MALE INCONTINENCE DEVICE

[75] Inventor: Graham E. Steer, Fulham, United Kingdom

[73] Assignee: E. R. Squibb & Sons, Inc., Princeton, N.J.

[21] Appl. No.: 383,148

[22] Filed: Feb. 2, 1995

[30] Foreign Application Priority Data

Feb. 2, 1994 [GB] United Kingdom .................. 9401984

[51] Int. Cl.⁶ .................................................. A61F 5/44
[52] U.S. Cl. .......................... 604/349; 604/352; 128/844
[58] Field of Search .................................. 604/349–353; 128/842, 844, 917, 918

[56] References Cited

U.S. PATENT DOCUMENTS

| 4,187,851 | 2/1980 | Hauser | 604/352 |
| 4,540,409 | 9/1985 | Nystrom et al. | 604/349 |
| 5,336,211 | 8/1994 | Metz | 604/349 |
| 5,423,784 | 6/1995 | Metz | 604/349 |

*Primary Examiner*—Robert A. H. Clarke
*Attorney, Agent, or Firm*—Stuart E. Krieger

[57] ABSTRACT

An improved male incontinence comprises a condom located within a hollow tubular applicator open at both ends, in which a strip of tape having a medical grade adhesive on one surface and a release layer strip on the other surface is arranged in a helically wound configuration within the condom with the adhesive engaging the inner surface of the condom and the release layer strip located radially inwardly of the adhesive, there being a pull-cord or equivalent attached to a free end of the release layer strip so that upon removal thereof, the adhesive is exposed and can be brought into contact with the penis of the wearer in order to securely attach the device.

7 Claims, 2 Drawing Sheets

MALE INCONTINENCE DEVICE

This invention relates to a male incontinence device.

The literature is replete with designs for male incontinence devices. These designs aim to meet all or most of the following requirements:

1. comfortable to wear;
2. easy to apply to the penis;
3. security of attachment;
4. avoidance of leakage;
5. hygiene;
6. compact and durable.

Male incontinence devices based on, or including, a hollow condom-like rubber latex member, with an opening of about 35 to 50 mm. at one end and a drain outlet of lesser diameter, e.g. up to about 10 mm. at the other end, have been the subject of proposals in the patent literature for many years. Such a member is herein called a condom purely for brevity. Such members are also sometimes called external catheters. An early design is seen in British Patent No. 1,304,554 (Stillewerner). In this, the open end is rolled up into a convolution, and is unrolled when applied. Another condom is seen in British Patent No. 2,048,680 (Craig Medical). In British Patent No. 2,094,630 (Adair) there is a proposal for a rigid support rim in conjunction with a condom. A liner for mounting an external catheter on a penis is shown in British Patent No. 2,096,901 (Bard), and an alternative way of mounting is shown in British Patent No. 2,099,706 (Hollister). A sheath (for attachment to a penis) which is rolled upon itself and which has adhesive between successive rolls is disclosed in British Patent No. 2,106,784 (Mentor). A different approach to the task of applying a sheath to a penis is adopted in British Patent No. 2,120,102 (Bard) which shows a tubular sheath support which is moved along the sheath (the condom). Internal coating of a condom sheath with an adhesive layer is suggested in British Patent No. 2,198,952 (Hollister).

It is an aim of the present invention to provide an improved male incontinence device.

According to one aspect of the invention, there is provided a male incontinence device comprising a condom located within a hollow tubular applicator open at both ends, in which a strip of tape having a medical grade adhesive on one surface and a release layer strip on the other surface is arranged in a helically wound configuration within the condom with the adhesive engaging the inner surface of the condom and the release layer strip located radially inwardly of the adhesive, there being a pull-cord or equivalent attached to a free end of the release layer strip so that upon removal thereof, the adhesive is exposed and can be brought into contact with the penis of the wearer in order to securely attach the device.

The invention will be better understood from the following particular description of a preferred embodiment, given with reference to the accompanying drawings. In the drawings, like reference numbers denote like parts.

Figure 3:
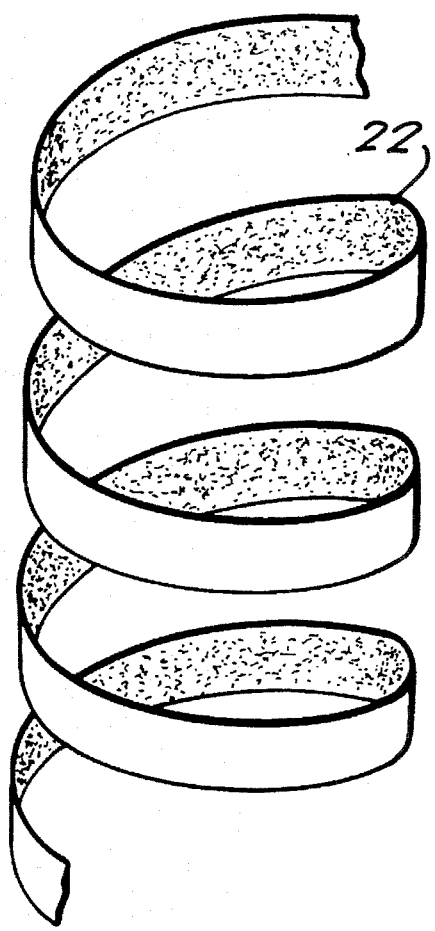
FIG. 3 is a diagrammatic illustration of a strip of adhesive tape, seen in the form of a pulled out helix, which has a sealable/resealable low tack adhesive on one of its surfaces, this tape being used to form the cover referred to above, which is located outside the condom prior to use.
Figure 1:
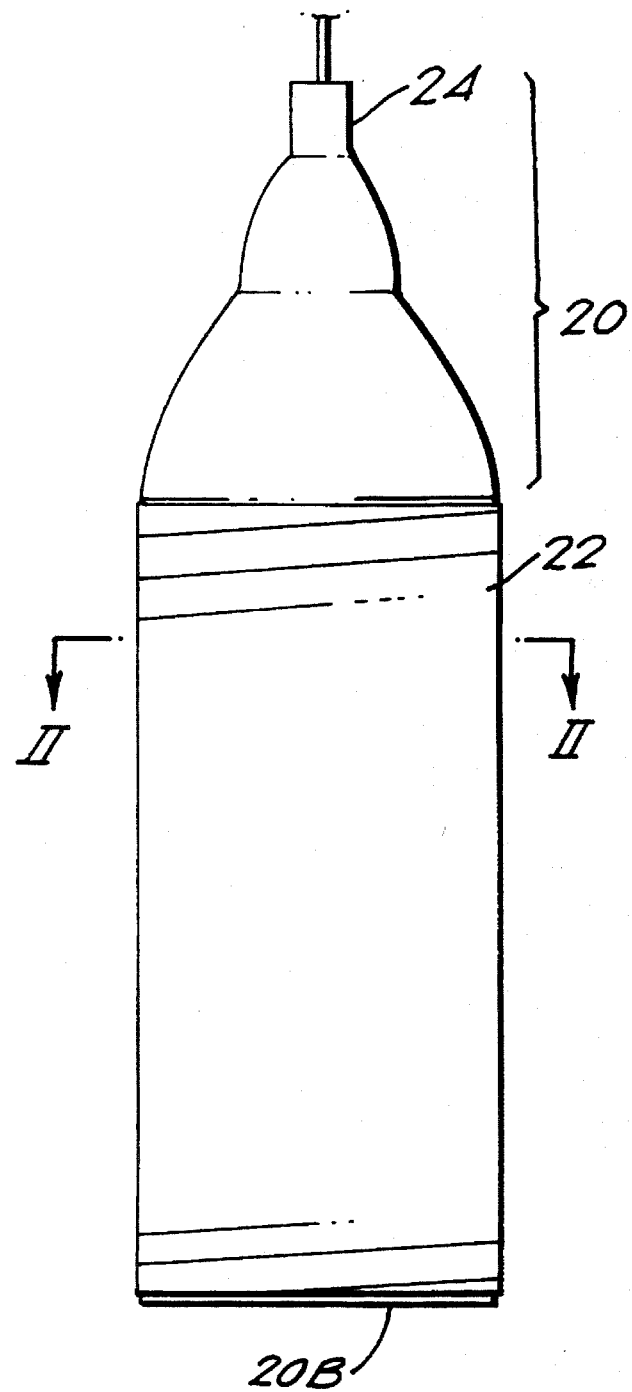
FIG. 1 illustrates a tubular body, acting as a cover for one example of male incontinence device according to the invention; this cover acts as a support for a condom therein.

Referring firstly to FIG. 1, this illustrates a tubular body which acts as an external cover and support for a condom serving as an external catheter. The cover is herein also called an applicator. An external supporting cover is provided since it makes application of the condom to a wearer particularly simple and effective. The supporting cover is made by winding a strip 22 (FIG. 3) over the outside of the condom 20. The adhesive strip 22 may be a fabric or plastics woven or non-woven strip, for example a 150 micron thick polyester or polypropylene plastic strip, or a thin cardboard strip, of which one side only is coated with a low tack sealable/resealable type adhesive such as can be obtained from the 3-M Company.

The adhesive strip 22 is helically wound over the outside of the condom 20, with the adhesive facing inwardly, and with successive turns of the strip in edge-butting relationship, or possibly slightly overlapping each other; and when wound, this wrap forms a substantially cylindrical tubular cover over most of the exterior of the condom 20. However, a portion 20B of the condom extends out of the generally cylindrical tube as seen in FIG. 1.

The condom 20 is preferably of thin polyurethane or synthetic rubber or, possibly, rubber latex, and has a drain outlet 20A at its free end. The outlet diameter may be up to about 10 mm., usually about 6 mm. The internal diameter of the layer end (20B) may be, for example, either 35 mm. or 50 mm. depending on the intended wearer. An adhesive strip 16 is arranged as a helix on the inner surface of the condom 20.

Figure 2:
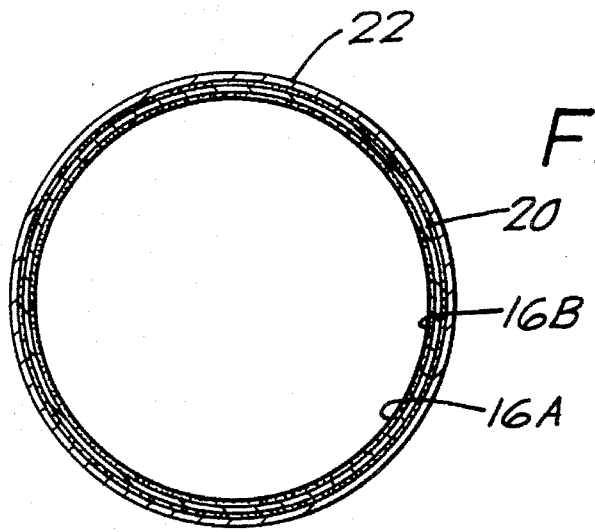
FIG. 2 is a cross section on the lines II—II of FIG. 1.
Figure 5:
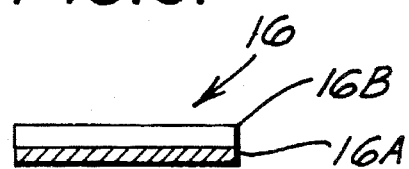
FIG. 5 is a cross-section through a tape which can be withdrawn from the interior of the condom, as illustrated in FIG. 4.

The adhesive strip 16 comprises a carrier strip upon one surface of which is placed a relatively high tack medical grade adhesive which may for example be a pressure sensitive acrylic adhesive or a hydro-colloid adhesive. The carrier strip is preferably a release paper or release plastics film which, once the adhesive is in contact with a suitable support or applicator, can be peeled off the adhesive. The adhesive strip 16 is seen in transverse cross-section in FIG. 5 and comprises adhesive 16B and a strip 16A of a release material, e.g. silicone coated paper. That is, inside the condom, the composite strip 16 has its adhesive layer 16B in contact with the interior surface of the condom 20, and on the inside of this winding of adhesive 16B there is the peel-off release strip 16A to which is attached a pull cord 16C. The strip 16 is spirally arranged over substantially the whole internal length of the condom 20. The assembly comprising the condom 20, the adhesive 16, and the external supporting tubular cover 22 is preferably packaged, by conventional packing machinery, in a "blister pack" or is otherwise conventionally hermetically sealed in a suitable container in such a way as to keep it sterile until the pack is opened and the male incontinence device is required for use. As seen in FIG. 2, which is a cross section on the generally horizontal plane II—II of FIG. 1, there is illustrated the outer cover 22 formed by the spirally wound second adhesive strip referred to in connection with FIGS. 1 and 3, this being readily removable from the condom 20 when the condom is to be applied to an incontinent person, because it is only attached thereto by a relatively low tack adhesive.

In use, the person requiring to wear the male incontinence device removes it from the blister pack and it is then applied over the penis. At this time, due to the attachment between the condom 20 and the cover 22, the condom is maintained with its internal diameter slightly larger than the patient's penis diameter. Even a very flaccid and/or partly withdrawn penis can be "scooped up" and brought within the condom 20 via its open end 20B, which is a significant advantage in that, unlike all male incontinence devices currently on the market known to the present Inventor, no direct handling of the penis by nurses is necessary. While holding the assembly against the body of the wearer, the pull cord 16C is then pulled, which peels off the release strip 16A so exposing the surface of the adhesive layer 16B, this surface being inwardly facing. Then, the wearer, or the nurse, can gently squeeze the outer cylindrical tube 22 bringing the adhesive 16B firmly but comfortably into contact with the penis. The pull cord 16C and cover layer 16A attached thereto is then discarded, and the spiral wrap 22 is also unwrapped and discarded. Suitable tubing is attached to the condom outlet 20A to conduct away urine to a leg bag or other suitable container.

Figure 4:
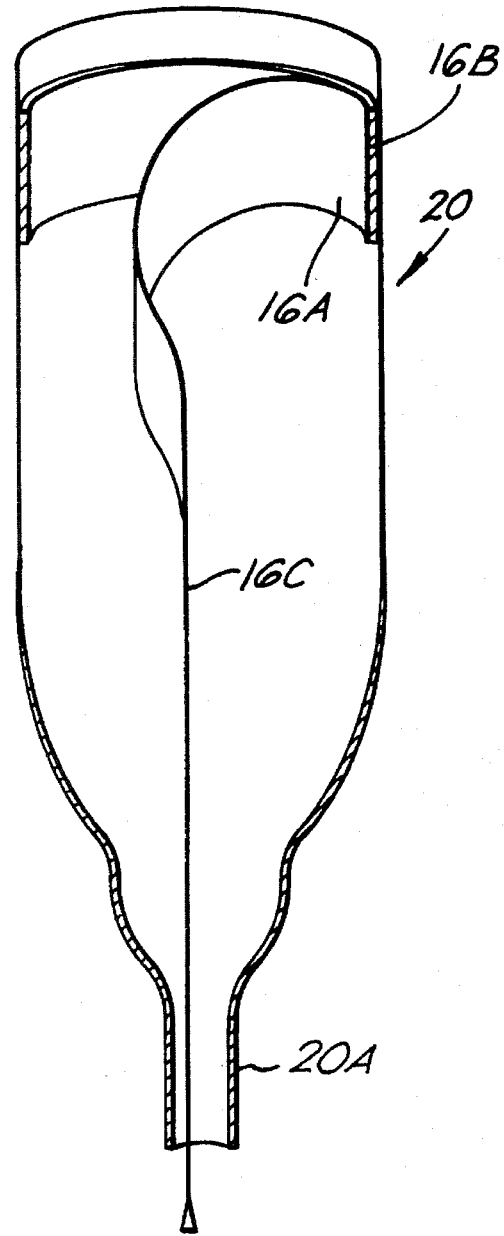
FIG. 4 is a view of the male incontinence device, partly cut away, showing its outlet and a pull cord arranged to permit withdrawal of successive turns of a release paper strip covering an adhesive that has been applied to the internal surface of the condom.

As seen in FIG. 4, the release strip 16A and pull cord 16C attached to the end thereof are shown with the release strip partly pulled off.

While a preferred embodiment of the present invention has been particularly described and illustrated herein, it will be understood that changes and modifications can be made, without departing from the invention. It is believed that among the main advantages of the present male incontinence device are that it can be readily manufactured using well tried established techniques, that it can be applied to patients, particularly elderly or hospitalised patients, who have flaccid penises in a simple, quick and effective manner without the nurse having to directly handle the penis, and that the adhesive coating internally of the condom is more uniformly and securely applied than can be obtained with condoms in which unrolling operations are employed to transfer adhesive from the exterior surface to the interior surface of the condom. To the best of the present Inventor's knowledge and belief, no male incontinence device currently on the market provides all of these advantages.

It is anticipated that male incontinence devices according to the present invention will be made in a plurality of sizes, as may be needed by the prospective wearers, for example, a so-called "normal" or standard size device may have an internal diameter (other than at the urine outlet) in its unstretched condition of about 35 mm. and a larger size may have an internal diameter of say 50 mm.

I claim:

1. A male incontinence device comprising:

a condom having an inner and outer surface;

a strip of tape having two opposite surfaces with a medical grade adhesive on one surface and a release layer strip on the other surface, said strip of tape being helically wound and adhered to the inner surface of said condom; and a pull cord member attached to an end of said release layer strip, said release layer strip being removable upon pulling said pull cord member so as to expose the medical grade adhesive and facilitate adhesion of the condom to the male wearer.

2. The device according to claim 1 wherein said medical grade adhesive is a relatively high-tack adhesive.

3. The device according to claim 1 wherein said medical grade adhesive is a pressure-sensitive acrylic.

4. The device according to claim 1 wherein said medical grade adhesive is a hydrocolloid adhesive.

5. The device according to claim 1 wherein said applicator is formed by wrapping an adhesive strip around the outside of the condom, said seal bearing a low-tack sealable/resealable adhesive.

6. The device according to claim 5 wherein said low-tack adhesive is carried by a polypropylene or polyester strip.

7. A combination of the male incontinence device of claim 1 and a hollow tubular applicator wherein, the applicator is open at both ends, said condom being located at least partly within said applicator.

* * * * *